(12) United States Patent
Scarberry et al.

(10) Patent No.: US 8,714,153 B2
(45) Date of Patent: May 6, 2014

(54) METHOD FOR SELECTING A DEVICE ADAPTED TO TREAT DISORDERED BREATHING

(75) Inventors: Eugene N. Scarberry, Trafford, PA (US); Michael T. Kane, Harrison City, PA (US); Benjamin Shelly, Pittsburgh, PA (US)

(73) Assignee: RIC Investments, LLC, Wilmington, DE (US)

( * ) Notice: Subject to any disclaimer, the term of this patent is extended or adjusted under 35 U.S.C. 154(b) by 1538 days.

(21) Appl. No.: 12/054,698

(22) Filed: Mar. 25, 2008

(65) Prior Publication Data

US 2008/0251075 A1    Oct. 16, 2008

Related U.S. Application Data

(60) Provisional application No. 60/923,637, filed on Apr. 16, 2007.

(51) Int. Cl.
*A62B 7/00* (2006.01)
*A61M 16/00* (2006.01)

(52) U.S. Cl.
USPC .................................. 128/204.23; 128/204.18

(58) Field of Classification Search
CPC ..................... A61M 16/00; A61M 2016/0021; A61M 2016/0039; A61M 2016/0036; A61M 16/06; A61M 16/0666; A61M 2016/0672; A61M 2230/40; A62B 7/00; A62B 7/02; A61B 1/267; A61B 5/08; A61B 5/0803

USPC ............ 128/200.24, 204.18–205.26, 206.21, 128/206.28–206.29, 207.13, 207.19

See application file for complete search history.

(56) References Cited

U.S. PATENT DOCUMENTS

| | | |
|---|---|---|
| 5,279,304 A | 1/1994 | Einhorn et al. |
| 5,316,002 A | 5/1994 | Jackson et al. |
| 5,458,137 A | 10/1995 | Axe et al. |
| 5,704,345 A | 1/1998 | Berthon-Jones |
| 5,743,256 A | 4/1998 | Jalowayski |
| 5,817,028 A | 10/1998 | Anderson |

(Continued)

OTHER PUBLICATIONS

Zhao et al.; Effect of Anatomy on Human Nasal Air Flow and Odorant Transport Patterns: Implications for Olfaction; J. Chemical Senses, vol. 29, No. 5, pp. 365-379, 2004.

*Primary Examiner* — Rachel Young
(74) *Attorney, Agent, or Firm* — Michael W. Haas (57) ABSTRACT

A method for selecting a device adapted to treat disordered breathing includes determining a number of characteristics associated with at least a portion of the airway of a patient, comparing each of at least some of the number of characteristics to a corresponding threshold, and selecting such a device in response to the comparison. An alternative method for selecting a device adapted to treat disordered breathing includes delivering a flow of breathing gas to the airway of a patient, determining a minimum effective therapeutic pressure associated with such patient, and selecting, relative to the minimum effective therapeutic pressure, an oral appliance or one of a number of patient interface devices.

20 Claims, 8 Drawing Sheets

(56) References Cited

U.S. PATENT DOCUMENTS

| | | |
|---|---|---|
| 5,884,622 A | 3/1999 | Younes |
| 6,425,395 B1 | 7/2002 | Brewer et al. |
| 6,565,517 B1 | 5/2003 | Rasmussen |
| 6,715,485 B1 | 4/2004 | Djupesland |
| 6,793,629 B2 | 9/2004 | Rapoport et al. |
| 6,910,479 B1 * | 6/2005 | Van Brunt ............... 128/204.18 |
| 7,100,608 B2 | 9/2006 | Brewer et al. |
| 2002/0020412 A1 * | 2/2002 | Gilbert et al. ............ 128/203.12 |
| 2003/0172936 A1 * | 9/2003 | Wilkie et al. ............ 128/207.18 |
| 2004/0149289 A1 | 8/2004 | Djupesland |
| 2004/0200476 A1 | 10/2004 | Bamford |
| 2005/0092321 A1 * | 5/2005 | Aylsworth et al. ....... 128/200.24 |
| 2005/0257788 A1 | 11/2005 | Aylsworth et al. |
| 2006/0060198 A1 | 3/2006 | Aylsworth et al. |
| 2007/0272240 A1 * | 11/2007 | Aylsworth et al. ....... 128/204.18 |
| 2011/0192400 A9 * | 8/2011 | Burton et al. ............ 128/204.23 |

* cited by examiner

METHOD FOR SELECTING A DEVICE ADAPTED TO TREAT DISORDERED BREATHING

CROSS REFERENCE TO RELATED APPLICATIONS

This application claims priority under 35 U.S.C. §119(e) from provisional U.S. patent application No. 60/923,637 filed Apr. 16, 2007 the entire contents of which are incorporated herein by reference.

BACKGROUND OF THE INVENTION

1. Field of the Invention

The present invention pertains generally to the treatment of disordered breathing, and more particularly, to selecting a device adapted to treat a patient who suffers from disordered breathing.

2. Description of the Related Art

It is well known that many individuals suffer from disordered breathing during sleep. Obstructive sleep apnea (OSA), which affects millions of people throughout the world, is a common example of such disordered breathing. OSA is a condition in which sleep is repeatedly interrupted by an inability to breathe. This inability to breathe is typically caused by intermittent obstruction of a person's airway. Obstruction of the airway is believed to be due, at least in part, to a general relaxation of the muscles which stabilize the upper airway segment. When these muscles relax, the surrounding tissues collapse thereby obstructing the airway.

Those afflicted with OSA experience sleep fragmentation and intermittent cessation of ventilation during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of OSA include right ventricular dysfunction, carbon dioxide retention during sleep, as well as wakefulness, and continuous reduced arterial oxygen tension. Sleep apnea sufferers may be at risk for excessive mortality from these factors as well as by an elevated risk for accidents while driving and/or operating potentially dangerous equipment.

A person may suffer from the adverse effects discussed above even where only partial obstruction of the airway occurs. Partial obstruction of the airway typically results in shallow breathing referred to as a hypopnea. Other types of disordered breathing include upper airway resistance syndrome (UARS) and vibration of the airway, such as vibration of the pharyngeal wall, commonly referred to as snoring. It is also known that snoring can accompany closure of the airway leading to UARS, hypopnea, or apnea. Thus, snoring serves as an indicator that the patient is experiencing abnormal breathing.

Milder cases of disordered breathing may be treated using an oral appliance such as a mandibular advancement device (MAD). A MAD is generally structured to pull a patient's lower jaw (mandible) forward relative to their upper jaw (maxilla), which in turn, opens the patient's airway.

More severe cases of disordered breathing may be treated by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's effort, to increase the comfort to the patient. One such pressure support technique is referred to as bi-level pressure support (e.g., BiPAP® bi-level pressure support), in which the inspiratory positive airway pressure (IPAP) delivered to the patient is higher than the expiratory positive airway pressure (EPAP) delivered to the patient. Other pressure support therapies and/or ventilation therapies are known and employed for the treatment of disordered breathing.

Pressure support and ventilation therapies may be non-invasively delivered to the patient. A patient interface device, generally placed on the face of a patient, facilitates the delivery of a flow of breathing gas from a pressure/flow generating device (e.g., a ventilator, pressure support device, etc.) to the airway of the patient. Patient interface devices include nasal prongs, nasal masks, full nasal/oral masks, and total face masks, among others. The pressure of the flow of breathing gas delivered to the patient is generally derived through a titration process administered by a sleep technician. The pressure at which the flow of breathing gas is delivered, herein referred to as the "therapeutic pressure", is generally between 4 cm $H_2O$ and 40 cm $H_2O$, although other pressures may be employed.

Patient comfort is maximized by providing the flow of breathing gas at a minimum effective therapeutic pressure (i.e., at the minimum pressure necessary to keep the patient's airway open). Furthermore, adverse conditions (for example and without limitation, mask leakage, skin breakdown caused by mask over-tightening, and acrophage) may be avoided at lower therapeutic pressures. Improved patient compliance with the prescribed therapy is achieved by increasing patient comfort and decreasing the likelihood that the patient experiences adverse conditions.

The device selected to treat disordered breathing (e.g., an oral appliance or a patient interface device) is an important component for ensuring patient compliance and adequate treatment outcomes. For example, the type and/or style of the patient interface device selected is an important component for insuring patient compliance and for insuring that the minimum effective therapeutic pressure is prescribed to the patient. The flow of gas supplied to a patient encounters resistance associated with, for instance, the patient's nasal cavity and/or oral cavity. These resistances may vary from patient to patient. A patient suffering from a number of intra-nasal pathological conditions (such as and without limitation, deviated septum, polyps, hypertrophic turbinates and spurs, trauma, congenital problems, sinus infections, etc.) may have a high nasal resistance. If a nasal mask is the type selected for such a patient, the minimum effective therapeutic pressure that must be prescribed to overcome the patient's elevated nasal resistance may be relatively high. However, if a nasal/oral mask is the type selected, the minimum effective therapeutic pressure may be relatively low because the patient will also be able to breathe through his/her mouth, thus bypassing the elevated nasal resistance. Prescribing a lower minimum effective therapeutic pressure increases the likelihood that the patient will comply with his/her therapy.

Applicant is unaware of any prior art methods in which one or more characteristics of the patient's airway (and/or the effects on breathing caused by these characteristics) are considered during the selection of an appropriate device for treating disordered breathing.

Accordingly, a need exists for a method of selecting the appropriate device for treating disordered breathing and which overcomes these and other problems associated with known methods.

SUMMARY OF THE INVENTION

In accordance with an aspect of the present invention, a method for selecting a device adapted to treat disordered breathing comprises determining a number of characteristics associated with at least a portion of the airway of a patient, comparing each of at least some of the number of characteristics to a corresponding threshold, and selecting a device adapted to treat disordered breathing in response to the comparing step.

According to another aspect of the present invention, a method for selecting a device adapted to treat disordered breathing comprises delivering a flow of breathing gas to the airway of a patient, determining a minimum effective therapeutic pressure associated with such patient, and selecting, relative to the minimum effective therapeutic pressure, an oral appliance or one of a number of patient interface devices.

According to another aspect of the present invention, a method for selecting a device adapted to be worn by a patient comprises delivering a flow of breathing gas to the airway of a patient, applying perturbations adapted to cause oscillations in the flow of breathing gas delivered to the airway of such patient, measuring the effect, on the oscillations in the flow of breathing gas, caused by a number of characteristics associated with at least a portion of the airway of such patient, and responsive to the measuring step, selecting the device adapted to be worn by such patient.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Directional phrases used herein, such as, for example, left, right, clockwise, counterclockwise, top, bottom, up, down, and derivatives thereof, relate to the orientation of the elements shown in the drawings and are not limiting upon the claims unless expressly recited therein.

As employed herein, the term "number" shall mean one or more than one and the singular form of "a", "an", and "the" include plural referents unless the context clearly indicates otherwise.

As employed herein, the statement that two or more parts are "connected" or "coupled" together shall mean that the parts are joined together either directly or joined together through one or more intermediate parts. Further, as employed herein, the statement that two or more parts are "attached" shall mean that the parts are joined together directly.

Figure 1:
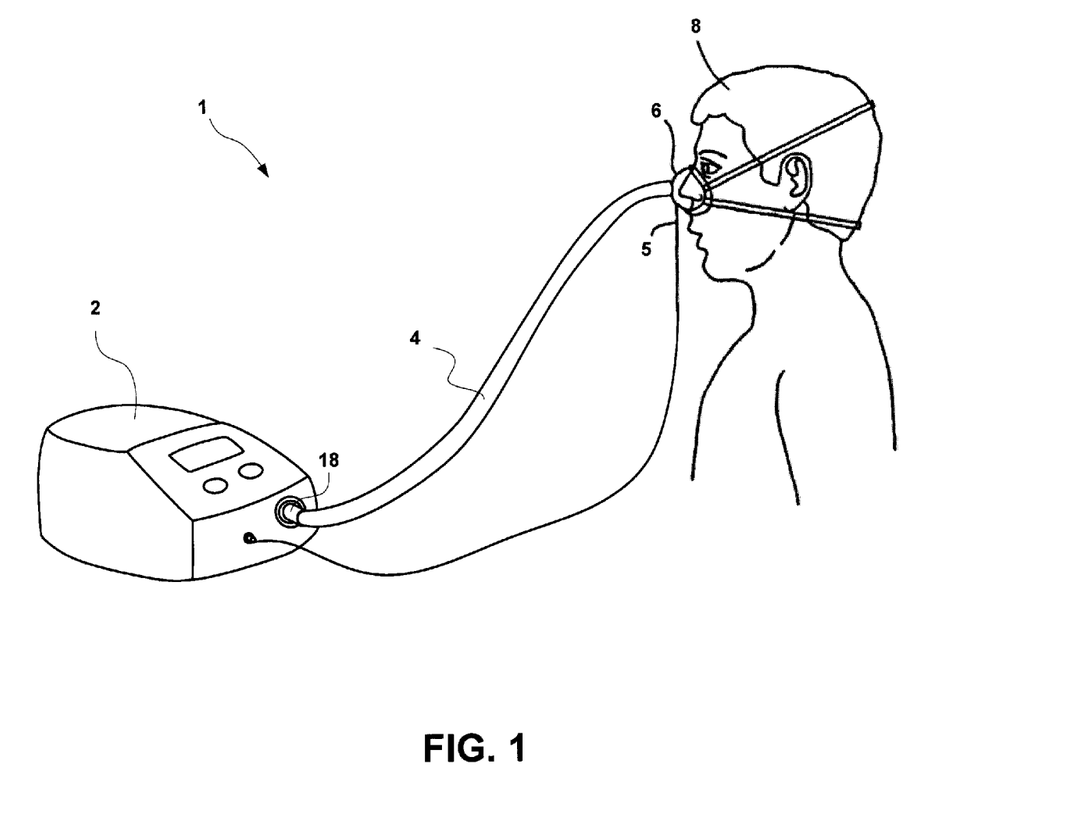
FIG. 1 is a schematic view of a system for selecting a device adapted to treat disordered breathing according to one embodiment of the present invention.

A system 1 for delivering a flow of breathing gas to a patient according to one embodiment is shown in FIG. 1. System 1 includes a flow generator 2, a patient circuit 4, and a patient interface device 6.

Flow generator 2 is structured to generate a flow of breathing gas which is communicated from outlet 18, through patient circuit 4, through patient interface device 6, and to the airway of patient 8. Although it is contemplated that other devices may be used, a REMstar® M Series therapy device available from Respironics, Inc. of Murrysville, Pa. is employed as the flow generator 2 in the current embodiment. Additionally, although a nasal mask is illustrated as being used in FIG. 1, it is contemplated that other types of patient interface devices (e.g., nasal prongs; full oral/nasal masks; total face masks; etc.) may be employed while remaining within the scope of the present invention.

In the current embodiment, patient interface device 6 includes a number of sensors (not shown) for measuring, without limitation, the pressure and flow rate of the breathing gas delivered to the airway of patient 8 and/or the pressure and flow rate of the gas exhaled by patient 8. The sensor(s) communicate with flow generator 2 via a signal line 5. Although illustrated as communicating via a hard-wired connection, it is contemplated that the number of sensors may wirelessly communicate with flow generator 2 while remaining within the scope of the present invention. Additionally, other sensors may be used in lieu of or in combination with the number of sensors associated with the patient interface device. A manometer, for example and without limitation, inserted into the patient's mouth, may be employed to obtain a pressure reading.

Figure 2:
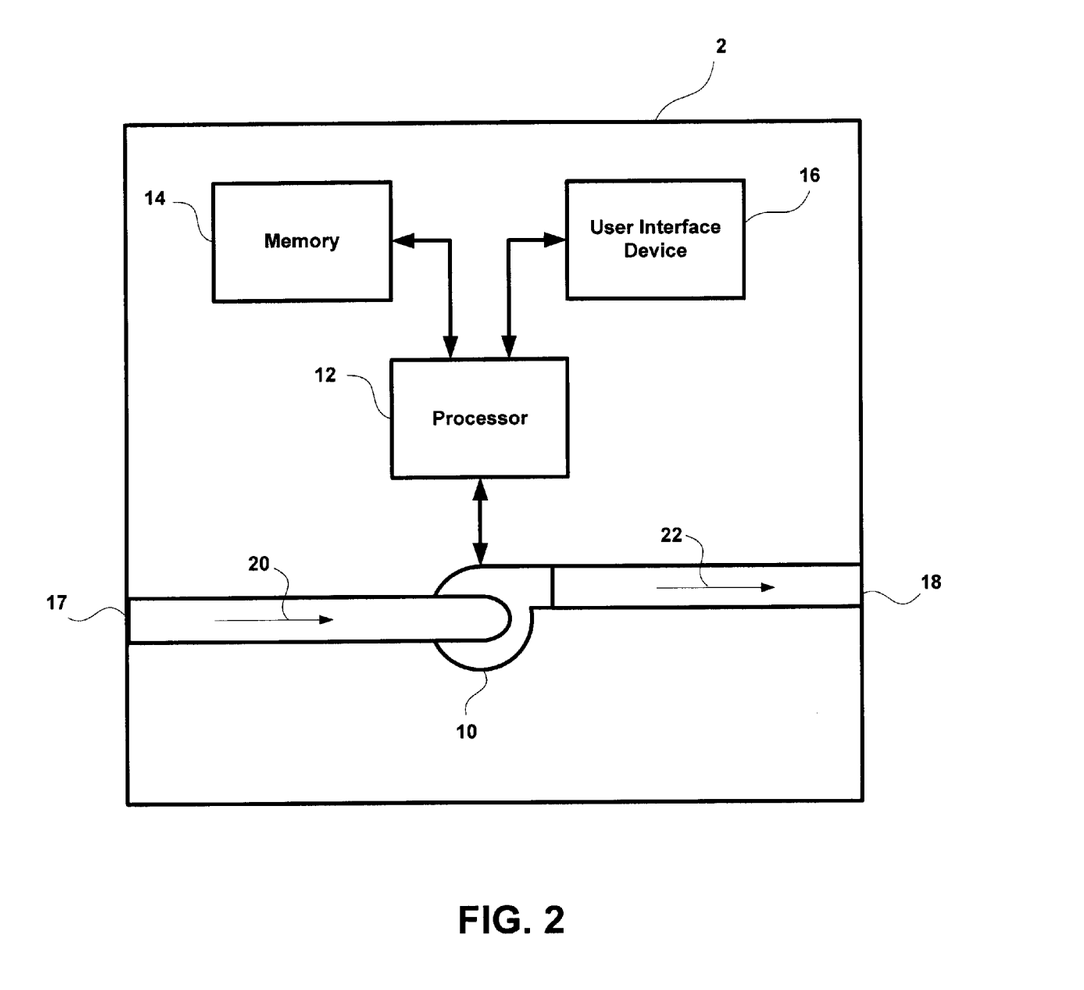
FIG. 2 is a block diagram illustrating the components of a flow generator for the system shown in FIG. 1 according to one embodiment.

FIG. 2 is a block diagram illustrating several components of flow generator 2 according to one embodiment. Flow generator 2 includes a blower 10, a processor 12, a memory 14, and a user interface device 16, among others. Blower 10 is structured to receive air (as indicated by arrow 20) from an inlet 17, pressurize the air, and provide a flow of breathing gas (as indicated by arrow 22) to outlet 18.

Generally, processor 12 is adapted to implement a number of routines associated with generating the flow of breathing gas. The routines may be in any of a variety of forms such as, without limitation, software, firmware, and the like which are executable by processor 12. For example, processor 12 may be adapted to implement a routine for producing control signals which direct blower 10 to provide continuous positive airway pressure (CPAP), a bi-level flow of gas (e.g., Bi-PAP® therapy), and/or additional functionalities (e.g., Bi-Flex® therapy; C-Flex™ therapy; forced oscillation output; etc.).

Memory 14 can be any of a variety of types of internal and/or external storage media such as, without limitation, RAM, ROM, EPROM(s), EEPROMS(s), and the like that provide a register for data storage such as in the fashion of an internal storage area of a computer, and can be volatile memory or nonvolatile memory. Memory 14 provides storage for, among others, the number of routines executable by processor 12. User interface 16 may include, without limitation, a mouse, a keyboard, a keypad, and/or a display.

Although shown as discrete components in FIG. 2, it is contemplated that one or more of the devices and/or their functions may be combined into a single device while remaining within the scope of the present invention. For example, memory 14 may be incorporated into processor 12. Additionally, other components and/or functions may be included in flow generator 2 while remaining within the scope of the present invention.

Figure 3:
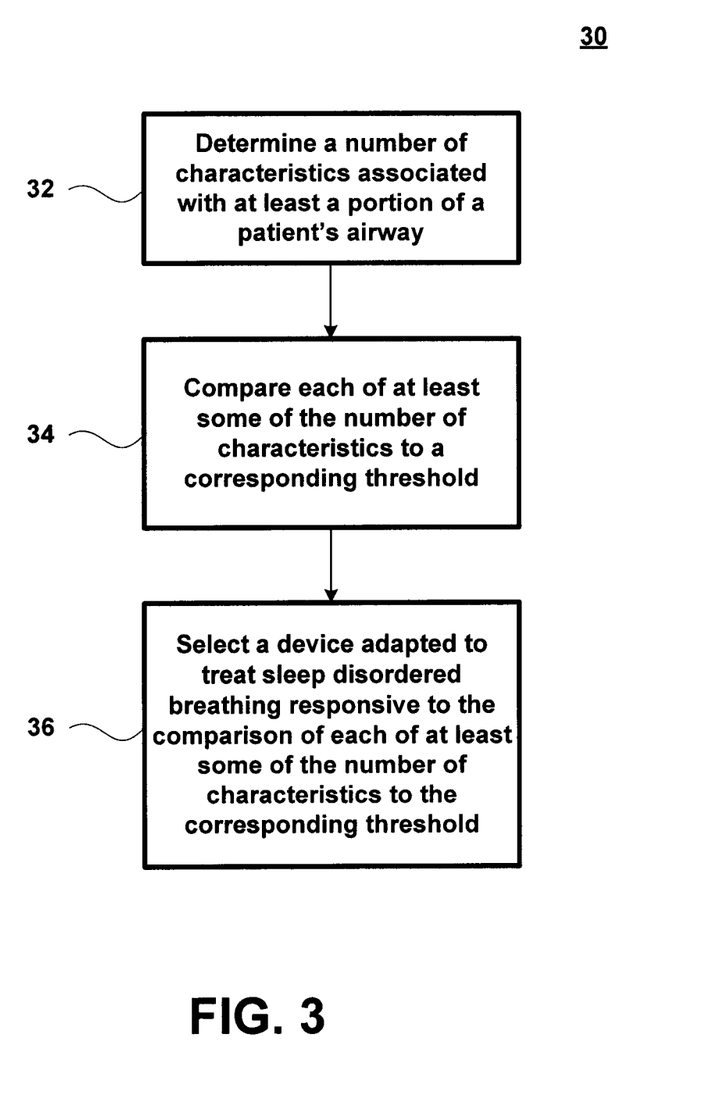
FIG. 3 illustrates an operational process for selecting a device adapted to treat disordered breathing according to one embodiment of the present invention.

FIG. 3 illustrates an operational process 30 for selecting a device adapted to treat disordered breathing according to one embodiment of the present invention. At operation 32, a number of characteristics associated with at least a portion of a patient's airway is determined. For example, the number of characteristics may include any number of pressure/flow attributes, nasal resistance, oral resistance, and/or a delta between an oral and nasal resistance, among others.

Figure 4:
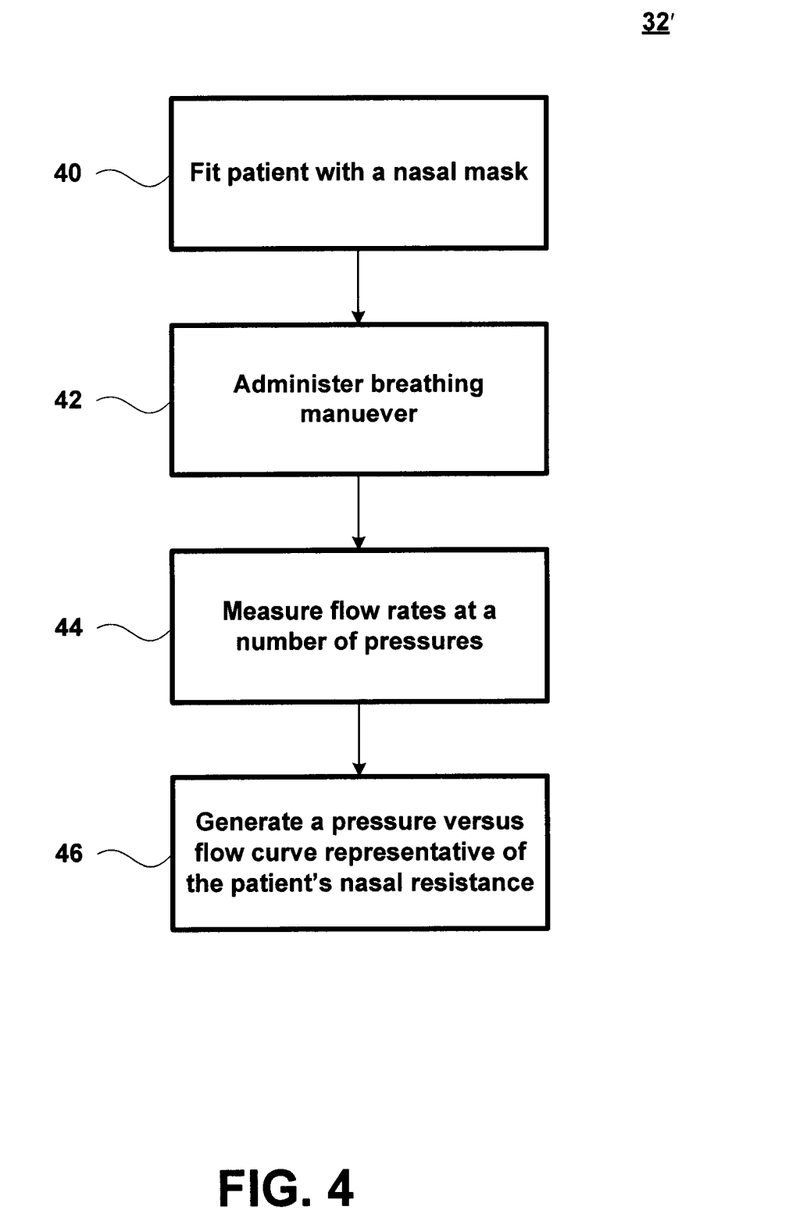
FIG. 4 illustrates an operational process for determining a number of characteristics associated with at least a portion of a patient's airway as shown in FIG. 3 according to a one embodiment of the present invention.

In a first embodiment of the present invention, as illustrated in FIG. 4, the nasal resistance between the patient's nares and the laryngopharynx is determined. The nasal resistance is determined by generating a pressure versus flow curve which is representative of the nasal resistance.

Referring to FIG. 4, the patient is fitted with a nasal mask in operation 40. In the current embodiment, the nasal mask has no leak and includes a pressure monitoring device (e.g., a pressure sensor) and a flow rate monitoring device (e.g., a flow sensor).

After the patient is fitted with the nasal mask, operational control passes to operation 42 where a breathing maneuver is administered to the patient. In the current embodiment, for example, the patient is instructed to open their mouth, open their glottis, and hold their breath while delivery of the flow of breathing gas is initiated.

After the patient completes the breathing maneuver, operational control passes to operation 44 where the pressure of the breathing gas delivered via the nasal mask is ramped up and the flow rates are measured at a number of pressures. In the current embodiment, for example, system 1 is employed to deliver the breathing gas at pressures ranging from 0-40 cmH$_2$0 at 1 cmH$_2$0 increments; flow rate measurements are taken at each increment (i.e., at 0 cmH$_2$0; 1 cmH$_2$0; 2 cmH$_2$0; 3 cmH$_2$0; etc.).

At operation 46, the pressures and measured flow rates are used to generate a pressure versus flow curve. This curve is representative of the patient's nasal resistance. Although the nasal resistance was determined using a pressure/flow curve in the current embodiment, it is contemplated that other methods for measuring/determining the nasal resistance may be employed while remaining within the scope of the present invention.

Figure 5:
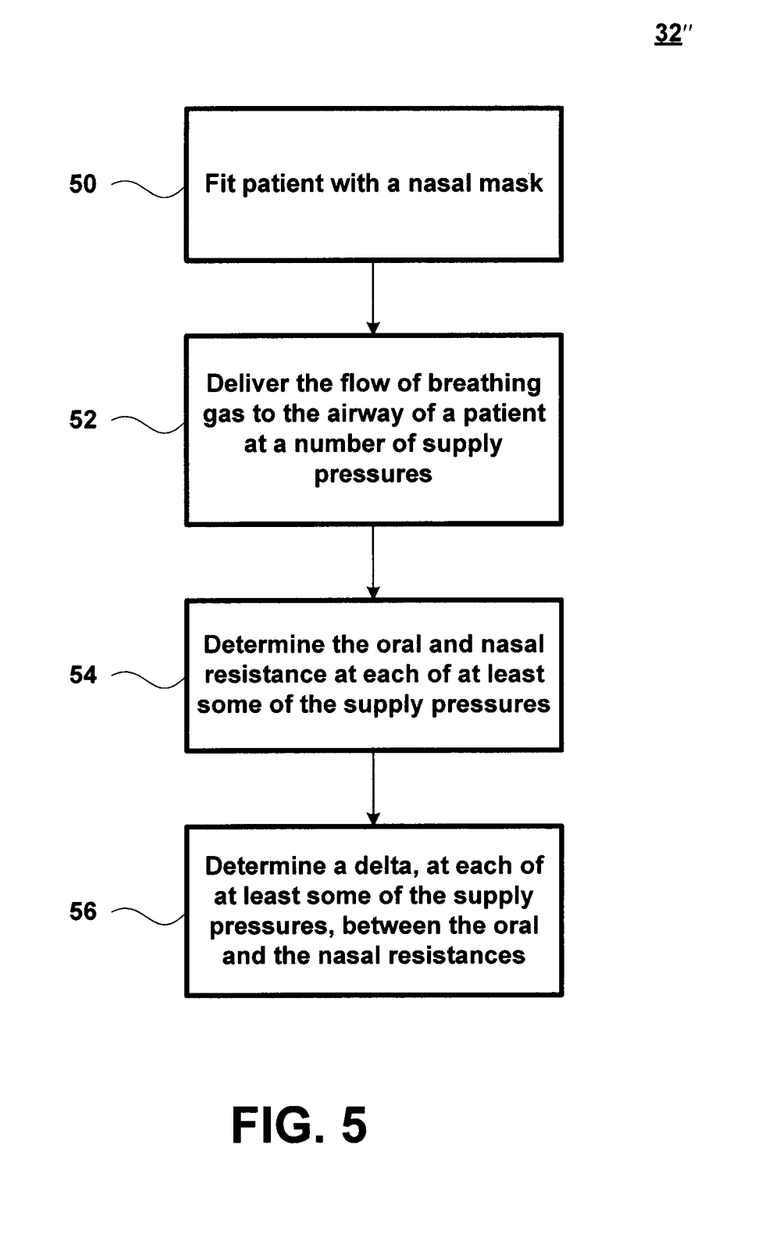
FIG. 5 illustrates an operational process for determining a number of characteristics associated with at least of portion of a patient's airway as shown in FIG. 3 according to another embodiment of the present invention.

In a second embodiment of the present invention, as illustrated in FIG. 5, a number of deltas each associated with the oral resistance between the patient's lips and laryngopharynx and the nasal resistance between the patient's nares and the laryngopharynx is determined. Referring to FIG. 5, the patient is fitted with a nasal/oral mask at operation 50. In the current embodiment, the nasal/oral mask has no leak and includes a pressure monitoring device (e.g., a pressure sensor) and a flow rate monitoring device (e.g., a flow sensor).

After the mask is fitted in operation 50, operational control passes to operation 52 where the flow of gas is delivered to the patient at a number of supply pressures. In the current embodiment, for example, the breathing gas is delivered at pressures ranging from 0-40 cmH$_2$0.

At operation 54, the patient's oral and nasal resistances are determined at each of at least some of the number of supply pressures. In the current embodiment, the oral and nasal resistances are determined at 5 cmH$_2$0 intervals (i.e., at 0 cmH$_2$0; 5 cmH$_2$0; 10 cmH$_2$0; etc.).

It is contemplated that any suitable method for determining the oral and/or nasal resistance (e.g., forced oscillation; rhinometry; nasal peak flow measurement; etc.) may be employed while remaining within the scope of the present invention. The nasal resistance, for example, may be determined by inserting a manometer into the patient's closed mouth, instructing the patient to breathe though his/her nose, and measuring the difference between the pressure at the patient's nares and the pressure at the patient's mouth. Likewise, the oral resistance may be measured by sealing the area around the patient's nares (e.g., with a mask having a manometer coupled thereto), instructing the patient to breathe through his/her mouth, and measuring the difference between the pressure at the patient's mouth and the pressure at the patient's nares. In yet another method, the patient is fitted with a nasal mask, a flow of gas at a know pressure is applied at the patient's nares, the patient holds his/her breath and opens his/her mouth to allow the flow of gas to exit their mouth, and the pressure/flow characteristics are plotted.

After determining the oral and nasal resistances, operational control passes to operation 56 where a delta between the oral resistance and the nasal resistance, at each of the at least some of the number of supply pressures, is determined. For example in the current embodiment, a delta is determined at each of 0 cmH$_2$0 (i.e., $\Delta_0$), 5 cmH$_2$0 (i.e., $\Delta_5$) ... 40 cmH$_2$0 (i.e., $\Delta_{10}$).

Returning to FIG. 3, after the number of characteristics associated with at least a portion of the patient's airway is determined in operation 32, operational control then passes to operation 34 where each of at least some of the number of characteristics are compared to a corresponding threshold.

In the first embodiment, for example, the corresponding threshold is selected based upon the nasal resistance of an average adult which is approximately 2 cmH$_2$O/L/S. A corresponding threshold that is, for instance, 100 percent greater than the nasal resistance of the average adult is selected. Accordingly in this example, the corresponding threshold of 4 cmH$_2$O/L/S is selected.

In the second embodiment, as another example, a number of corresponding thresholds may be selected based upon a delta between the oral resistance and the nasal resistance at the specific pressure of the flow of breathing gas delivered to an average adult, which is approximately 2 cmH$_2$O/L/S. A corresponding threshold that is, for instance, 100 percent greater than the delta at a specific supply pressure for the average adult is selected. For example and without limitation, if the average patient has a delta of 2 cmH$_2$O/L/S when a flow of breathing gas is delivered at a pressure of 20 cmH$_2$O, a corresponding threshold of 4 cmH$_2$O/L/S is selected. Alternatively, each of the number of deltas (determined at a number of different supply pressures) may be compared to a single corresponding threshold, such as the mean delta between the oral resistance and the nasal resistance for all of the specific pressures that the flow of breathing gas is delivered to the average adult.

Although discussed above as being selected based upon the nasal resistance of an average adult and/or upon the delta between the oral resistance and the nasal resistance of an average adult, it is contemplated that the corresponding threshold may be selected based on other criteria/characteristics. For example, and without limitation, it is contemplated that selection of the corresponding threshold may be based on the minimum effective therapeutic pressure associated with a particular patient. The minimum effective therapeutic pressure refers to the minimum pressure necessary for the flow of gas to keep that patient's airway splinted open.

After each of at least some of the number of characteristics is compared to the corresponding threshold in operation 34, operational control passes to operation 36 where a device adapted to treat disordered breathing is selected in response to comparing the number of characteristics to a corresponding threshold.

In the first embodiment, for example, a first device (such as, without limitation, an oral appliance) is selected where the patient's nasal resistance is less than the corresponding threshold and a second device (such as, without limitation, a nasal/oral mask) is selected where the patient's nasal resistance is greater than the corresponding threshold.

In the second embodiment, a first device (such as, without limitation, a nasal mask) is selected where the delta between the patient's oral resistance and nasal resistance (at a number of specific supply pressures) is less than a corresponding threshold (at the number of specific supply pressures) and a second device (such as, without limitation, a nasal/oral mask) is selected where the delta between the patient's oral resistance and nasal resistance (at the number of specific supply pressures) is greater than the corresponding thresholds (at the number of specific supply pressures).

Although operation 34 was only discussed in conjunction with a single threshold, it is contemplated that "a corresponding threshold" may also refer to any number of thresholds while remaining within the scope of the present invention. With the first embodiment, for example, operation 34 may include multiple thresholds such that if the patient's nasal resistance is less than a first threshold, an oral appliance is selected. If the patient's nasal resistance is greater than the first threshold, but less than a second threshold, a nasal mask is selected. Furthermore, if the patient's resistance is greater than the second threshold, but less than a third threshold, a nasal/oral mask is selected.

Figure 6:
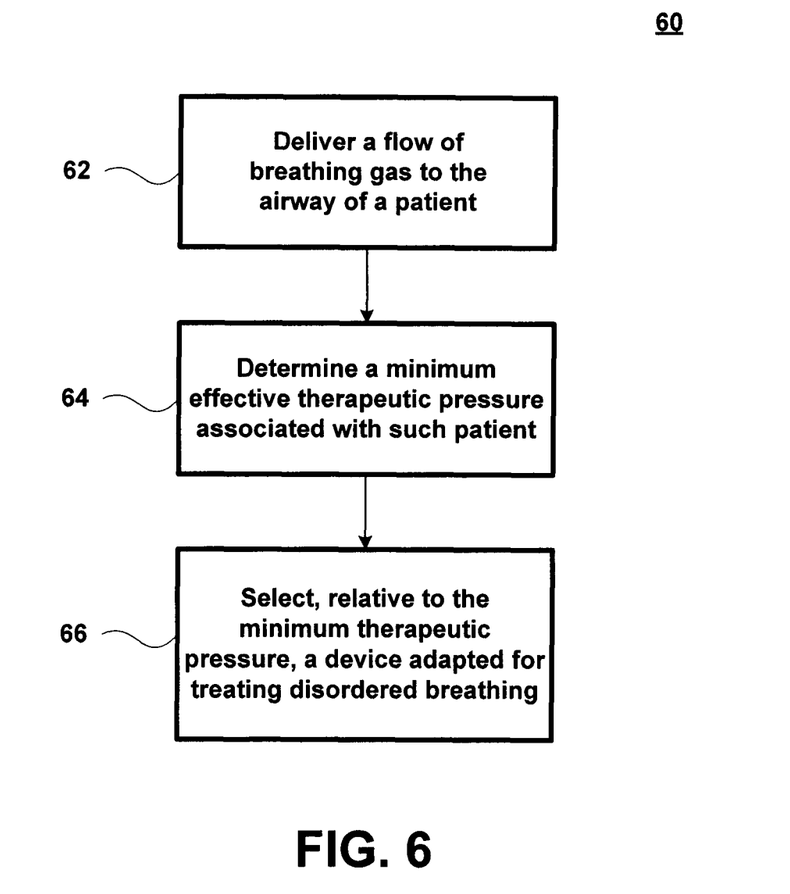
FIG. 6 illustrates an operational process for selecting a device adapted to treat disordered breathing according to another embodiment of the present invention.

FIG. 6 illustrates an operational process 60 for selecting a device adapted to treat disordered breathing according to a second embodiment of the present invention. At operation 62, a flow of breathing gas is delivered to the airway of a patient. In the current embodiment, system 1 is employed to deliver the breathing gas to the airway of the patient.

At operation 64, the minimum effective therapeutic pressure associated with such patient is determined. In current embodiment, polysomnography monitoring is used to determine the minimum effective therapeutic pressure associated with the patient. The polysomnography monitoring may be completed in any convenient location, such as in a sleep lab or in the patient's home, among others. Although discussed in conjunction with polysomnography monitoring, it is contemplated that other processes/methods may be employed to determine the minimum effective therapeutic pressure associated with the patient while remaining within the scope of the present invention.

After the minimum effective therapeutic pressure is determined in operation 64, a device adapted to treat sleep disordered breathing is selected in response to the minimum effective therapeutic pressure associated with the patient. In the current embodiment, for example and without limitation, if the minimum effective therapeutic pressure is substantially equal to atmospheric pressure, an oral appliance (such as a mandibular advancement device) is selected; if the minimum effective therapeutic pressure is between approximately 4-15 cmH$_2$O a nasal mask is selected; and if the minimum effective therapeutic pressure is between approximately 15-30 cmH$_2$O a full-face mask is selected.

Figure 7:
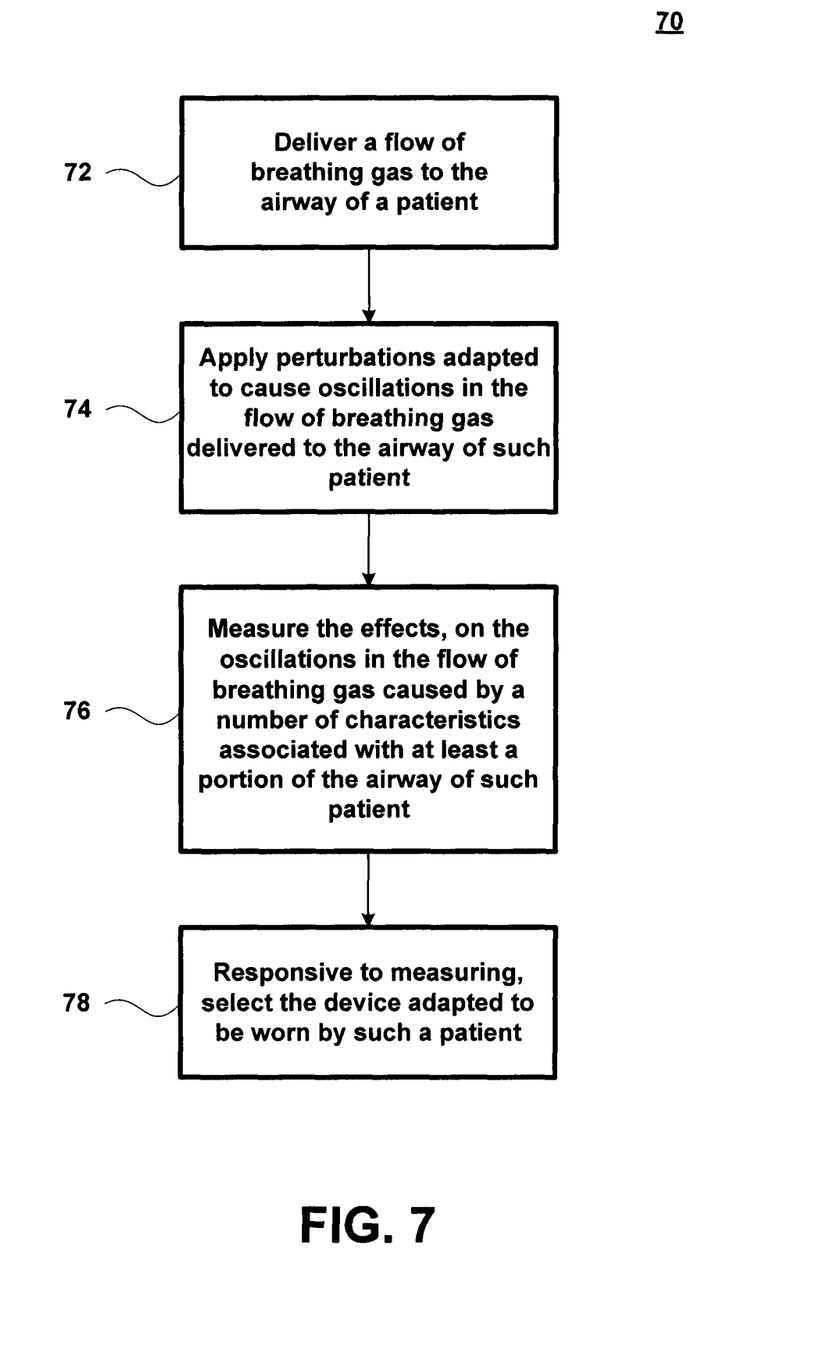
FIG. 7 illustrates an operational process for selecting a device adapted to treat disordered breathing according to another embodiment of the present invention.

FIG. 7 illustrates an operational process 70 for selecting a device adapted to treat sleep disordered breathing according to a third embodiment of the present invention. At operation 72, a flow of breathing gas is delivered to the airway of a patient. In the current embodiment, for example and without limitation, system 1 is employed to deliver a flow of continuous positive air pressure breathing gas.

At operation 74, perturbations adapted to cause oscillations in the flow of breathing gas delivered to the airway of the patient are applied. In the current embodiment, processor 12 is adapted to implement a routine for producing control signals which direct blower 10 to implement a forced oscillation technique (i.e., to cause oscillations in the amplitude of the flow breathing gas).

Operational control then passes to operation 76 where the effects on the oscillations in the flow of breathing gas caused by a number of characteristics associated with at least a portion of the patient's airway are measured. For example, it has been found that a patient's nasal resistance has a dampening effect on the oscillations provided in the flow of breathing gas. Generally, the greater the nasal resistance, the greater the dampening effect on the oscillations in the flow of breathing gas. Thus, by determining the amount of dampening, the nasal resistance associated with the patient's airway can be determined.

Operational control then passes to operation 78 where, responsive to operation 76, the device adapted to be worn by the patient is selected. In the current embodiment, for example, if the effects on the oscillations in the flow of breathing gas cause by a number of characteristics associated with at least a portion of the patient's airway are slight, a first device (such as a nasal mask) is selected. If, on the other hand, the effects on the oscillations in the flow of breathing gas cause by a number of characteristics associated with at least a portion of the patient's airway are substantial, a different device (such as a full nasal/oral mask) is selected.

Figure 8:
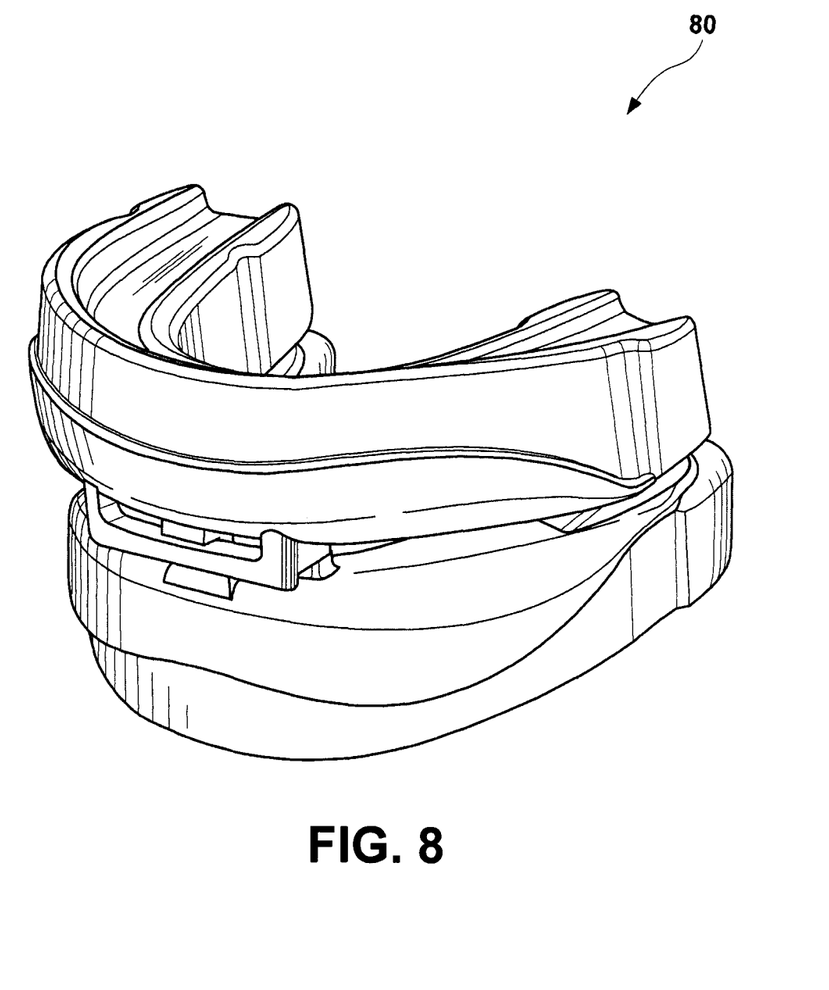
FIG. 8 is a perspective view of an oral appliance adapted to treat disordered breathing according to one embodiment of the present invention.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For instance, although discussed in context of selecting a desirable patient interface for delivery of a flow of breathing gas, it is contemplated that operational process 30 can easily be adapted for selecting other devices used to treat disordered breathing. For example, operational process 30 may be adapted such that an oral appliance, such as mandibular advancement device (MAD) 80 shown in FIG. 8, is selected when the flow resistance value associated with the patient is below the corresponding threshold.

What is claimed is:

1. A method for selecting a device adapted to treat sleep disordered breathing, the method comprising:
    fitting a patient with a first device, the first device being adapted to measure one or more resistance characteristics associated with at least a portion of an airway of the patient;
    determining from the first device a number of the resistance characteristics associated with at least the portion of the airway of the patient;

comparing each of at least some of the number of the resistance characteristics to a corresponding threshold; and selecting a second device in response to the comparing step, the second device being adapted to treat sleep disordered breathing, wherein selecting the second device comprises choosing one device from among a group consisting of at least two of a mandibular advancement device, nasal prongs, a nasal mask, a full nasal/oral mask structured to cover the patient's mouth and nose, and a total face mask, wherein each device of the group is chosen over another device in the group based at least in part on the comparison of the resistance characteristics to the threshold.

2. The method of claim 1, wherein determining the number of resistance characteristics associated with at least of portion of the airway comprises determining at least one pressure/flow attribute associated with a portion of the airway between the nares and the laryngopharynx of the patient.

3. The method of claim 2, wherein the first device is a nasal mask, and wherein determining the at least one pressure/flow attribute associated with the portion of the airway between the nares and the laryngopharynx of the patient comprises:

supplying a flow of gas to the patient via the nasal mask; and measuring the pressure/flow attributes of the flow of gas entering the patient's nares and exiting the patient's mouth.

4. The method of claim 1, wherein determining the number of resistance characteristics associated with at least of the portion of the airway comprises determining a nasal resistance associated with a portion of the airway between the nares and the laryngopharynx of the patient.

5. The method of claim 4, wherein determining the nasal resistance comprises:

providing a breathing gas at a number of different pressures;

measuring a flow rate of the breathing gas at each of at least some of the number of different pressures;

generating a pressure-flow curve from the measured flow rates and the number of different pressures; and correlating the pressure-flow curve to the nasal resistance associated with the portion of the airway.

6. The method of claim 4, wherein determining the nasal resistance comprises:

inserting a manometer into a closed mouth of the patient; and measuring the difference between the pressure present at the patient's nares and the pressure present at the patient's mouth when the patient breathes though their nose.

7. The method of claim 1, wherein comparing each of at least some of the number of resistance characteristics to the corresponding threshold further comprises:

determining a minimum effective therapeutic pressure associated with the patient; and selecting the threshold relative to the minimum effective therapeutic pressure.

8. A method for selecting a device adapted to treat sleep disordered breathing, the method comprising:

determining a number of characteristics associated with at least a portion of the airway of a patient;

comparing each of at least some of the number of characteristics to a corresponding threshold; and selecting a device adapted to treat sleep disordered breathing in response to the comparing step, wherein determining the number of characteristics associated with at least the portion of the airway comprises calculating a number of deltas between an oral resistance and a nasal resistance of the patient.

9. The method of claim 8, wherein comparing each of at least some of the number of characteristics to the corresponding threshold comprises comparing each of at least some of the number of deltas to the corresponding threshold.

10. The method of claim 8, wherein calculating the number of deltas between the oral resistance and the nasal resistance of the patient further comprises:

delivering a flow of breathing gas at a number of supply pressures;

determining an oral resistance and a nasal resistance for the patient at each of at least some of said number of supply pressures; and finding the difference between the oral resistance and a first nasal resistance at each of said number of supply pressures.

11. The method of claim 10, wherein delivering the flow of gas at the number of supply pressures includes delivering the flow of gas at atmospheric pressure and delivering the flow of gas at least one pressure higher than atmospheric pressure.

12. The method of claim 8, wherein determining the nasal resistance comprises:

inserting a manometer into a closed mouth of the patient; and measuring the difference between the pressure present at the patient's nares and the pressure present at such patient's mouth when the patient breathes though their nose.

13. The method of claim 8, wherein determining the oral resistance comprises:

fitting the patient with a nasal mask having a manometer associated therewith; and measuring the difference between the pressure present at the patient's mouth and the pressure present at the patient's nares while the patient breathes through their mouth.

14. A method for selecting a device adapted to treat sleep disordered breathing, the method comprising:

fitting a patient with a first device, the first device being adapted to measure one or more resistance characteristics associated with at least a portion of an airway of the patient;

determining from the first device a number of the resistance characteristics associated with at least the portion of the airway of the patient;

comparing each of at least some of the number of characteristics to a corresponding threshold; and selecting a second device from a group of two or more devices in response to the comparing step, the second device being adapted to treat sleep disordered breathing, wherein each device of the group is chosen over another device in the group based at least in part on the comparison of the resistance characteristics to the threshold.

15. The method of claim 14, wherein determining the number of resistance characteristics associated with at least of portion of the airway comprises determining at least one pressure/flow attribute associated with a portion of the airway between the nares and the laryngopharynx of the patient.

16. The method of claim 15, wherein the first device is a nasal mask, and wherein determining the at least one pressure/flow attribute associated with the portion of the airway between the nares and the laryngopharynx of the patient comprises:

supplying a flow of gas to the patient via the nasal mask; and measuring the pressure/flow attributes of the flow of gas entering the patient's nares and exiting the patient's mouth.

17. The method of claim 14, wherein determining the number of resistance characteristics associated with at least of the portion of the airway comprises determining a nasal resistance associated with a portion of the airway between the nares and the laryngopharynx of the patient.

18. The method of claim 17, wherein determining the nasal resistance comprises:

providing a breathing gas at a number of different pressures;

measuring a flow rate of the breathing gas at each of at least some of the number of different pressures;

generating a pressure-flow curve from the measured flow rates and the number of different pressures; and correlating the pressure-flow curve to the nasal resistance associated with the portion of the airway.

19. The method of claim 17, wherein determining the nasal resistance comprises:

inserting a manometer into a closed mouth of the patient; and measuring the difference between the pressure present at the patient's nares and the pressure present at the patient's mouth when the patient breathes though their nose.

20. The method of claim 14, wherein comparing each of at least some of the number of resistance characteristics to the corresponding threshold further comprises:

determining a minimum effective therapeutic pressure associated with the patient; and selecting the threshold relative to the minimum effective therapeutic pressure.

* * * * *